(12) United States Patent
Ogawa

(10) Patent No.: US 6,783,494 B2
(45) Date of Patent: Aug. 31, 2004

(54) ULTRASONIC PROBE AND ULTRASONIC DIAGNOSING APPARATUS USING THE SAME

(75) Inventor: Eiji Ogawa, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/244,445

(22) Filed: Sep. 17, 2002

(65) Prior Publication Data

US 2003/0060708 A1 Mar. 27, 2003

(30) Foreign Application Priority Data

Sep. 27, 2001 (JP) ........................................ 2001-296376

(51) Int. Cl.[7] .............................................. A61B 8/00
(52) U.S. Cl. .................................................... 600/437
(58) Field of Search .............................. 600/437, 443; 73/643, 603, 606, 608, 597; 367/149; 356/493, 477, 479, 502; 348/769; 359/1, 7, 30, 32; 342/179

(56) References Cited

U.S. PATENT DOCUMENTS

| | | | | | |
|---|---|---|---|---|---|
| 3,836,950 | A | * | 9/1974 | Bhuta et al. ................... | 73/608 |
| 4,284,324 | A | * | 8/1981 | Huignard et al. ............... | 359/7 |
| 5,080,491 | A | * | 1/1992 | Monchalin et al. .......... | 356/493 |
| 5,353,262 | A | * | 10/1994 | Yakymyshyn et al. ....... | 367/149 |
| 5,384,573 | A | * | 1/1995 | Turpin ......................... | 342/179 |
| 5,450,752 | A | * | 9/1995 | White et al. .................... | 73/643 |
| 5,566,133 | A | * | 10/1996 | Engeler et al. ................ | 367/11 |
| 5,748,564 | A | * | 5/1998 | Pattanayak ................... | 367/149 |
| 5,796,003 | A | * | 8/1998 | Sandhu et al. ................. | 73/603 |
| 5,814,730 | A | * | 9/1998 | Brodeur et al. ................ | 73/597 |
| 5,909,279 | A | * | 6/1999 | Pepper et al. ................ | 356/479 |
| 6,501,551 | B1 | * | 12/2002 | Tearney et al. .............. | 356/477 |

OTHER PUBLICATIONS

Beard et al. An optical detection system for biomedical photoacoustic imaging. Jan. 2000. pp. 100–109.*
Beard et al. 2D line–scan photoacoustic imaging of absorbers in a scattering tissue phantom. Jan. 2001. pp. 34–42.*
Department of Medical Physics and Bioengineering. 2D optical ultrasound array.*
Takahashi, et al. "Underwater Acoustic Sensor with Fiber Bragg Grating." Optical Review, vol. 4, No. 6, pp. 691–694, 1997.
Uno, et al. "Fabrication and Performance of a Fiber Optic Micro–Probe for Megahertz Ultrasonic Field Measurements." T. IEE Japan, vol. 118–E, No. 11, pp. 487–492, 1998.

* cited by examiner

Primary Examiner—Marybeth Jones
Assistant Examiner—Ruby Jain
(74) Attorney, Agent, or Firm—Sughrue Mion, PLLC

(57) ABSTRACT

An ultrasonic probe for detecting ultrasonic waves in a two-dimensional manner without necessity of electric-wiring works to a large number of very fine elements and without increasing of crosstalk and electric impedance. The ultrasonic probe is equipped with an ultrasonic transmitting function and can be provided in low cost. The ultrasonic probe includes an ultrasonic detecting element having a reception plane capable of receiving ultrasonic waves, for modulating light on the basis of ultrasonic waves applied to respective positions of the reception plane, and at least one ultrasonic transmitting element for transmitting ultrasonic waves.

20 Claims, 10 Drawing Sheets

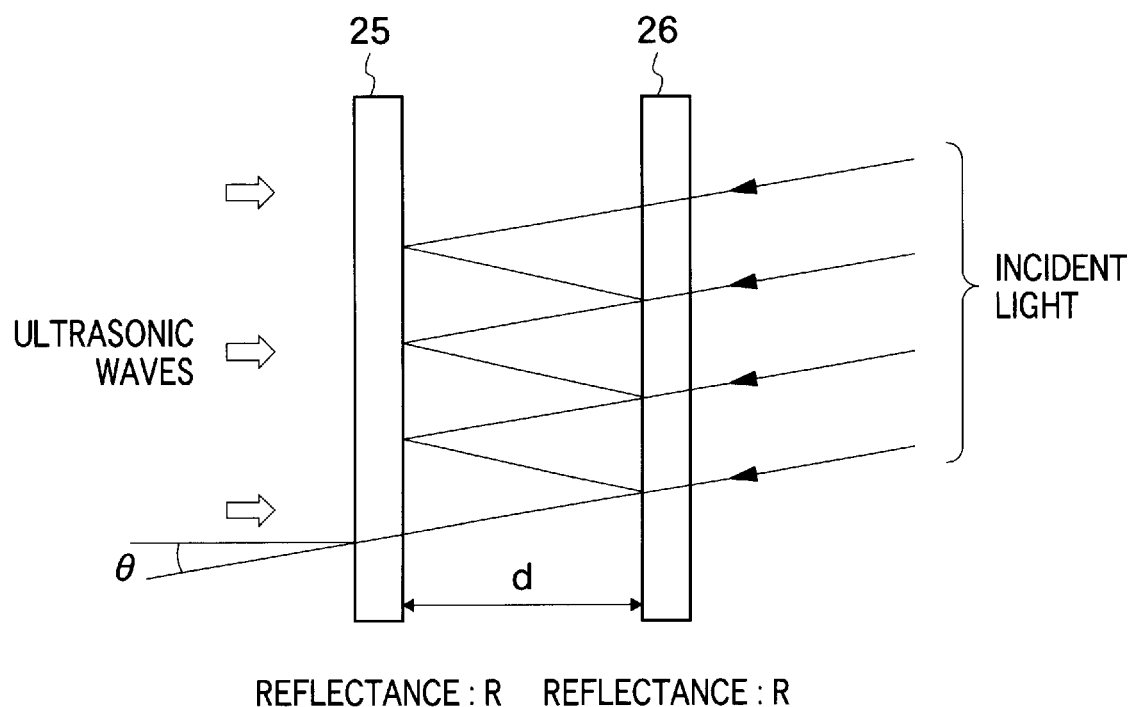

ULTRASONIC PROBE AND ULTRASONIC DIAGNOSING APPARATUS USING THE SAME

BACKGROUND OF THE INVENTION

1. Field of the Invention

The present invention generally relates to an ultrasonic probe for transmitting/receiving ultrasonic waves. More specifically, the present invention is directed to an ultrasonic diagnosing apparatus to be used in medical diagnoses by transmitting/receiving ultrasonic waves to/from biological bodies with employment of such an ultrasonic probe.

2. Description of a Related Art

In conventional ultrasonic diagnosing apparatus, while both ultrasonic transmitting means and ultrasonic receiving means use the same systems, one-dimensional sensor array is generally employed which includes elements (vibrators) for transmitting/receiving ultrasonic waves. The vibrators are realized by using piezoelectric ceramics which is typically known as PZT (Pb (lead) zirconate titanate), or by using a polymer piezoelectric element such as PVDF (polyvinyle difluoride). Furthermore, such a one-dimensional sensor array is mechanically moved so as to acquire two-dimensional images, and those two-dimensional images are synthesized with each other, so that a three-dimensional image is obtained.

However, since there is a time lag along the mechanically moving direction of the one-dimensional sensor array in accordance with this method, tomographic images acquired at different time instants are synthesized with each other, and therefore, the synthesized image becomes blurred. As a result, this conventional method is not suitable for imaging objects to be inspected such as living bodies, for instance, in such a case where ultrasonic echo observations are carried out by employing the above-described conventional ultrasonic diagnosing apparatus.

In order to acquire a three-dimensional image having a high image quality by using ultrasonic waves, a two-dimensional sensor array capable of acquiring a two-dimensional image without being mechanically moved is necessarily required. For this reason, such a method of manufacturing a two-dimensional sensor array with employment of the above-described PZT or PVDF has been considered. In such a case where the above-described PZT or PVDF is employed so as to manufacture such a two-dimensional sensor array, elements must be processed in very fine manners, and also, a very large number of very fine elements must be connected by using wiring lines. However, it is practically difficult to process these elements in a finer manner, and also to manufacture these elements in a higher integration, as compared with the presently-available very fine processing manner and element integration method.

Also, even when these problems could be solved, there are other problems. That is, crosstalk between elements would be increased, electric impedance of elements connected by very fine wiring lines would be increased which deteriorate an S/N ratio thereof, and electrode portions of these very fine elements would be easily destroyed. Under such a circumstance, it is practically difficult to realize such a two-dimensional sensor array with employment of PZT or PVDF elements.

On the other hand, as another ultrasonic sensor without using a piezoelectric material such as PZT, an optical detecting type sensor is known in this field, by which an optical fiber is utilized and an ultrasonic wave is converted into an optical signal to be detected. As such an optical detecting type ultrasonic sensor, the below-mentioned ultrasonic sensors are reported, namely, an optical detecting type sensor using the fiber Bragg grating (will be abbreviated as an "FBG" hereinafter) described in "Underwater Acoustic Sensor with Fiber Bragg Grating" written by TAKAHASHI et al. in National Defense Academy (Japan), see OPTICAL REVIEW Vol. 4, No. 6 in 1997, p. 691–694; and an optical detecting type sensor using the Fabry-Perot resonator (will be abbreviated as an "FPR" hereinafter) described in "Fabrication and Performance of a Fiber Optic Micro-Probe for Megahertz Ultrasonic Field Measurements" written by UNO et al. in Tokyo Institute of Technology, see T. IEE Japan, Vol. 118-E, No. 11 in 1998, p. 487–492.

If such a two-dimensional sensor array is manufactured by employing these ultrasonic sensors, there are such merits that electric-wiring works to a large number of very fine elements are no longer required, and furthermore, higher sensitivities can be obtained. However, this two-dimensional sensor owns another problem that since this sensor itself is made in high cost, manufacturing cost of such a two-dimensional sensor is increased, and also, manufacturing cost of an ultrasonic probe using the two-dimensional sensor array is increased. Also, since an optical detecting sensor is not inherently provided with an ultrasonic wave transmitting function, this optical detecting sensor requires such an ultrasonic transmitting function.

SUMMARY OF THE INVENTION

The present invention has been made to solve the above-described problems, and therefore, has a first object to provide an ultrasonic probe equipped with an ultrasonic transmitting function and capable of detecting an ultrasonic wave signal in a two-dimensional manner, without necessities of electric-wiring works to a large number of very fine elements and without increasing crosstalk and electric impedance, while the ultrasonic probe can be manufactured in low cost. Also, a second object of the present invention is to provide an ultrasonic diagnosing apparatus capable of acquiring either a two-dimensional ultrasonic image or a three-dimensional ultrasonic image by applying thereto the above-described ultrasonic probe.

To solve the above-explained problems, an ultrasonic probe according to one aspect of the present invention comprises: an ultrasonic detecting element having a reception plane capable of receiving ultrasonic waves, for modulating light on the basis of ultrasonic waves applied to respective positions of the reception plane; and at least one ultrasonic transmitting element for transmitting ultrasonic waves.

Also, an ultrasonic diagnosing apparatus according to one aspect of the present invention comprises: an ultrasonic probe including an ultrasonic detecting element having a reception plane capable of receiving ultrasonic waves, for modulating light on the basis of ultrasonic waves applied to respective positions of the reception plane, and a plurality of ultrasonic transmitting elements arranged around the reception plane of the ultrasonic detecting element, for transmitting ultrasonic waves in accordance with drive signals; a drive signal generating circuit for generating drive signals to be applied to the plurality of ultrasonic transmitting elements; a photodetector having a plurality of pixels, for detecting light output from corresponding positions of the ultrasonic detecting element to output detection signals; signal processing means for receiving detection signals output from the photodetector to process the received detection signals; control means for controlling both generation timing of the drive signals and reception timing of the detection signals; image processing means for constructing an image signal on the basis of an output signal of the signal processing means; and an image display unit for displaying thereon an image on the basis of the image signal.

According to the present invention, since the ultrasonic transmitting elements are arranged around, or inside the ultrasonic detecting element for modulating the light on the basis of the ultrasonic waves applied to the respective positions of the ultrasonic reception plane, the ultrasonic probe can detect the ultrasonic signals in a two-dimensional manner without increasing crosstalk and electric impedance, and furthermore, is capable of equipping the ultrasonic transmitting function, while this ultrasonic probe can be manufactured in low cost. As a consequence, the ultrasonic diagnosing apparatus capable of acquiring either the two-dimensional ultrasonic image or the three-dimensional ultrasonic image and having the better image qualities can be realized with employment of such an ultrasonic probe.

BRIEF DESCRIPTION OF THE DRAWINGS

A better understanding of the present invention will become apparent from a detailed description to be read in conjunction with the accompanying drawings, in which:

FIG. 1A is a front view for showing an internal structure within a housing of the ultrasonic probe, and FIG. 1B is a plan view for showing the internal structure within the housing of the ultrasonic probe;

FIG. 5 is a diagram for illustratively showing another ultrasonic detecting element which may be employed in the ultrasonic probe according to the first embodiment of the present invention;

FIG. 6A is a plan view for showing an internal structure within a housing of the ultrasonic probe having a single ultrasonic transmitting element, and FIG. 6B is a plan view for showing an internal structure within a housing of the ultrasonic probe having a plurality of ultrasonic transmitting elements;

DESCRIPTION OF THE PREFERRED EMBODIMENTS

Figure 1A:
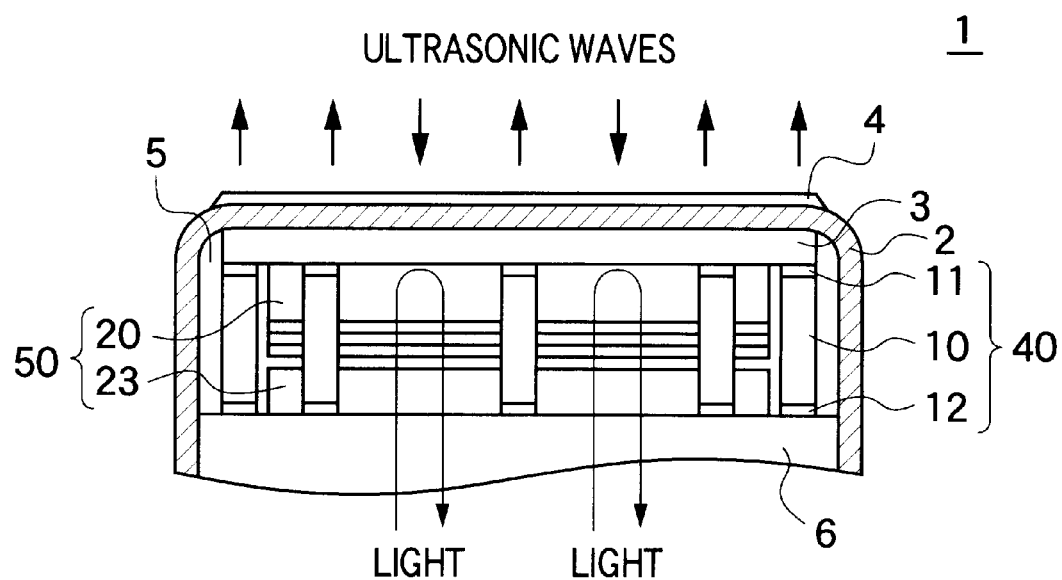
FIG. 1A and FIG. 1B are diagrams for schematically showing a structure of an ultrasonic probe according to a first embodiment of the present invention, i.e.

Referring now to drawings, various embodiments of the present invention will be described in detail. It should be understood that the same reference numerals are employed as those for showing the same, or similar structural elements, and explanations thereof are omitted.

First, a description will now be made of an ultrasonic probe 1 according to a first embodiment of the present invention. In this ultrasonic probe according to the first embodiment of the present invention, a plurality of ultrasonic transmitting elements (ultrasonic transducer elements) are arranged at a peripheral portion of a reception plane of an ultrasonic detecting element.

Figure 1B:
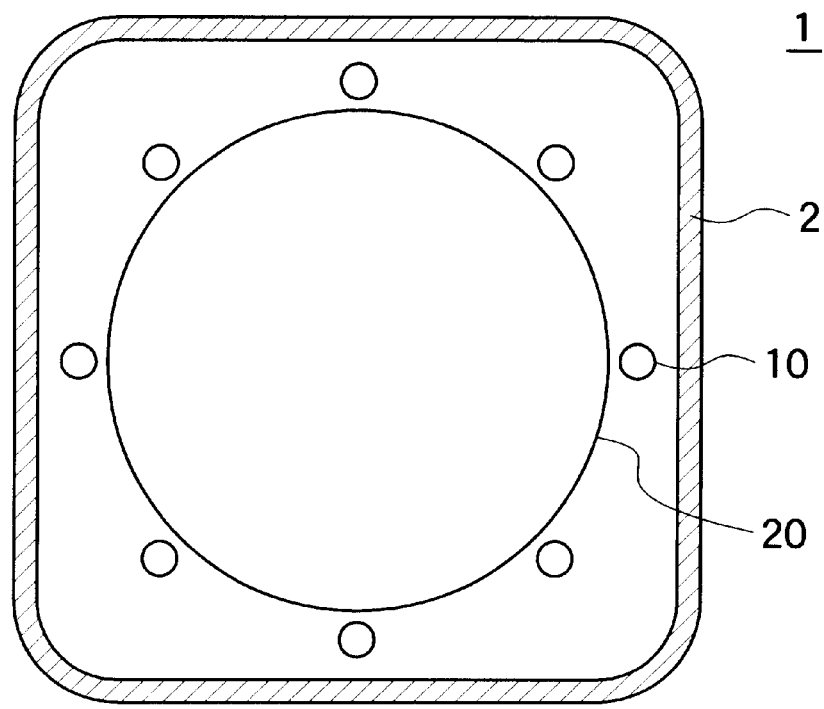

FIG. 1A and FIG. 1B are diagrams for schematically showing an entire structure of the ultrasonic probe according to the first embodiment of the present invention. FIG. 1A is a front view for showing an internal structure within a housing of the ultrasonic probe and FIG. 1B is a plan view for showing the internal structure within the housing of the ultrasonic probe. As shown in FIG. 1, both a plurality of ultrasonic transmitting units 40 and an ultrasonic detecting unit 50 are mounted into a housing 2 of this ultrasonic probe 1. Each ultrasonic transmitting unit 40 includes an ultrasonic transmitting element 10 and a plurality of electrodes 11, 12, whereas the ultrasonic detecting unit 50 includes an ultrasonic detecting element 20 and an optical fiber 23. The optical fiber 23 is employed in order that light emitted from a light source is entered into this optical fiber 23, and such light modulated by the ultrasonic detecting element 20 is projected to a photodetector.

In the ultrasonic transmitting unit 40, the ultrasonic transmitting element 10 is constructed of a material (piezoelectric element) having a piezoelectric characteristic. This piezoelectric element is realized by piezoelectric ceramics which is typically known as PZT (Pb(lead) zirconate titanate), or a polymer piezoelectric element such as PVDF (polyvinyle difluoride). When either a pulse-shaped voltage (drive signal) or a continuous-wave (CW) voltage (drive signal) is applied to such a piezoelectric element, this piezoelectric element produces very small mechanical vibrations. Since such mechanical vibrations are produced, either ultrasonic pulses or continuous-wave (CW) ultrasonic waves are generated from this piezoelectric element, and then, are propagated as ultrasonic beams through a propagation medium. The electrodes 11 and 12 are employed in order to apply drive signals to the ultrasonic transmitting elements 10.

An acoustic coupling layer 3 may be preferably provided among the ultrasonic transmitting elements 10, the ultrasonic detecting element 20, and the housing 2 in order to match acoustic impedance with each other. This acoustic matching layer 3 may be constituted by employing Pylex glass (registered trademark) or epoxy resin containing metal powder, by which ultrasonic waves may be easily propagated. Also, an acoustic lens material 4 such as silicone rubber may be preferably provided on a surface of the housing 2, while this acoustic lens material 4 also has a function capable of protecting both the ultrasonic transmitting elements 10 and the ultrasonic detecting element 20.

Furthermore, a sound absorbing material 5 may be filled in spaces between the adjoining ultrasonic transmitting elements 10 in order to reduce crosstalk of ultrasonic waves. As this sound absorbing material 5, epoxy resin containing metal powder, and also rubber containing ferrite powder may be suitably used. It should also be noted that an interior portion of the housing 2 is solidified by resin 6 except for areas in the vicinity of the ultrasonic transmitting elements 10 and the ultrasonic detecting elements 20.

Now, both a structure of the above-described ultrasonic detecting element 20 employed in the ultrasonic detecting unit 50 and a principle detecting idea of ultrasonic waves will be described in detail with reference to FIG. 2. In this embodiment, a multi-layer film sensor is employed as this ultrasonic detecting element 20.

Figure 2:
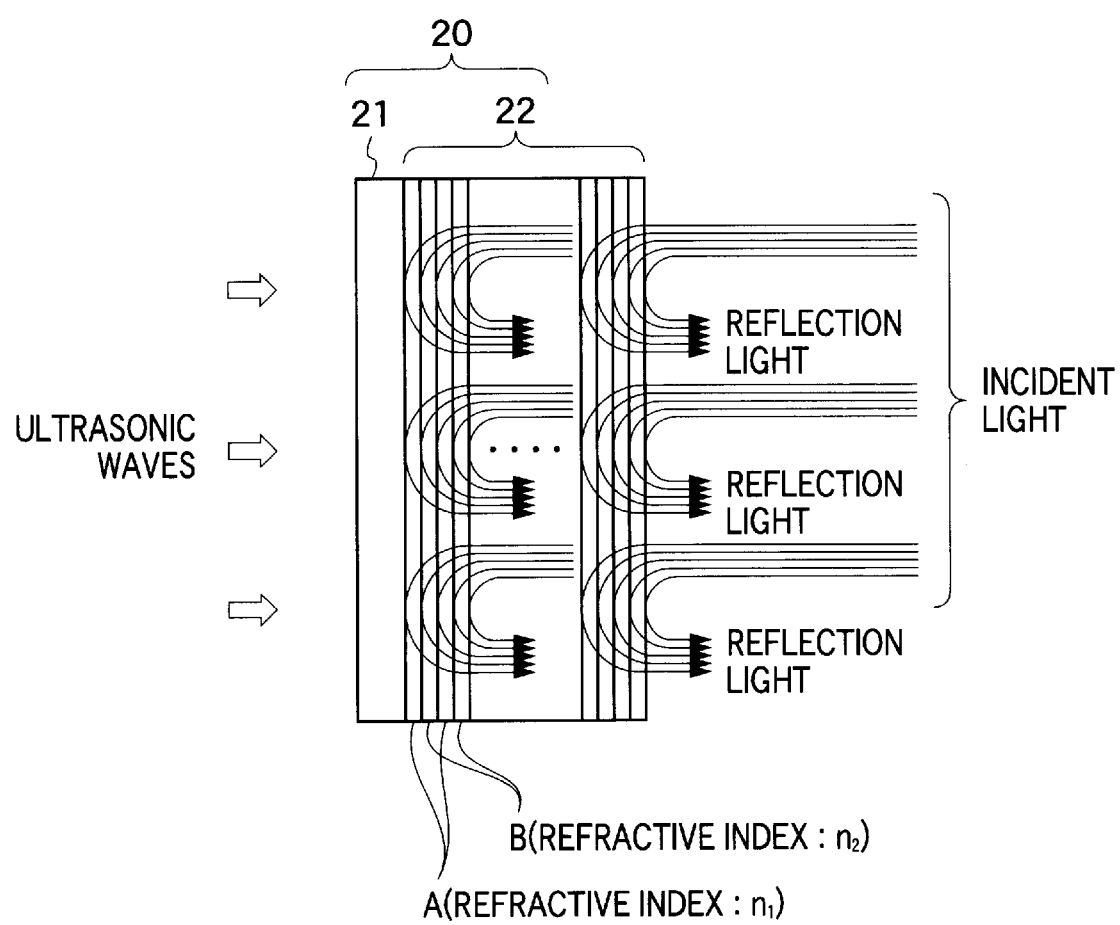
FIG. 2 illustratively shows an enlarged ultrasonic detecting element employed in the ultrasonic probe of the first embodiment.

In this ultrasonic detecting element (multi-layer film sensor) 20 as shown in FIG. 2, the base plate 21 is a film-shaped base plate which may produce distortion when ultrasonic waves (ultrasonic beams) are applied. This base plate 21 is shaped of, for example, a circle having a diameter of on the order of 2 cm or more. Two sorts of materials having different refractive indexes are alternately stacked on this base plate 21, so that the multi-layer film 22 having a Bragg grating structure is formed. In FIG. 2, there are shown a material layer "A" having a refractive index "$n_1$" and another material layer "B" having a refractive index "$n_2$".

Assuming now that a pitch (an interval) of a periodic structure of the multi-layer films 22 is equal to "d" and a wavelength of incident light is equal to "$\lambda$", the Bragg's reflection condition is expressed by the following expression:

$$2d \cdot \sin \theta = m\lambda \quad (1)$$

where symbol "m" is an arbitrary integer, and symbol "$\theta$" represents an incident angle of the incident light which is measured from an incident plane.

Assuming again that this incident angle "$\theta$" is equal to $\pi/2$, the Bragg's reflection condition is given by the following expression:

$$2d = m\lambda \quad (2)$$

The Bragg grating selectively reflects thereon such a light having a specific wavelength which satisfies the Bragg's reflection condition, and passes therethrough light having other wavelengths than the above-described specific wavelength.

When the ultrasonic waves are propagated through the ultrasonic detecting element 20, both the base plate 21 and the multi-layer film 22 are distorted in connection with this propagation of the ultrasonic waves, and thus, the pitch "d" of the periodic structure is changed at the respective positions of the multi-layer films 22. As a result, the wavelength "$\lambda$" of the incident light which is selectively reflected is changed. In a reflection characteristic of a Bragg grating, an inclined band where reflectance is varied is present before or after a center wavelength where the reflectance becomes the highest (namely, the transmittance becomes lowest). While such a detection light having a center wavelength which is located within the range of this inclined band is entered into the multi-layer films 22, the ultrasonic waves are applied to the multi-layer films 22. As a result, intensity changes of reflection light (otherwise the transmission light) in accordance with intensity of the ultrasonic waves at the respective positions of the ultrasonic wave receiving plane can be monitored. Since the intensity changes of the reflection light (or transmission light) are converted into intensity of ultrasonic waves, two-dimensional intensity distribution information of these ultrasonic waves can be acquired.

As a material of the above-described base plate 21, quartz glass ($SiO_2$), or optical glass such as BK7 (manufactured by Schott Glass) or the like may be employed. Also, as a substance used in the material layers "A" and "B", it is preferable to employ a combination of substances having refractive indexes which are different from each other by 10% or more. In other words, in the case of such a refractive index relationship of $n_1 < n_2$, such substances capable of satisfying $n_1 \times 1.1 \leq n_2$ are selected. This selection condition is to achieve a high reflectance at a boundary plane between the material layer "A" and the material layer "B". Also, both the material layers "A" and "B" are preferably made of such a material which can be easily expanded/compressed. This selection condition is to increase a distortion amount when ultrasonic waves are applied to the material layers "A" and "B", and eventually to increase a sensitivity of a system. As the combination of such substances capable of satisfying such conditions, for example, there is a combination of quartz glass ($SiO_2$) and a titanium oxide ($Ti_2O_3$). The refractive index of $SiO_2$ is nearly equal to 1.45, and the refractive index of $Ti_2O_3$ is nearly equal to 2.0 with respect to laser light having a wavelength of 1520 nm. This fact may sufficiently satisfy the above-described condition. That is, the refractive indexes of these materials are different from each other by 10% or more. Other than the above-described combination, another combination of quartz glass ($SiO_2$) and a tantalum oxide ($Ta_2O_5$) may be employed.

A layer thickness (film thickness) of the material layer "A" and a layer thickness (film thickness) of the material layer "B" are preferably selected to be approximately ¼ of the wavelength "$\lambda$" of the light which is entered into the multi-layer films 22. In this case, an expression "film thickness" implies an optical distance which is expressed by a product between a refractive index "n" of a material layer and a thickness "t" of this material layer. In other words, "$n \cdot t = \lambda/4$" may constitute the condition. As a consequence, the pitch of the periodic structure of the multi-layer film 22 may become nearly equal to ½ of the wavelength of the incident light, and the multi-layer films 22 may selectively reflect thereon the light having such a wavelength satisfying the above-described expression (2) of the Bragg's reflection condition, and also may pass therethrough the light having other wavelengths than the above-described wavelength. Also, either one or more material layer "a" having a layer thickness of approximately $\lambda/2$ or one or more material layer "B" having a layer thickness of approximately $\lambda/2$ may be alternately contained in selected portions of such a multi-layer film containing material layers "A" each having a layer thickness of approximately $\lambda/4$ and material layers "B" each having a layer thickness of approximately $\lambda/4$.

The above-described material layers "A" and "B" are stacked on the substrate 21 in such a manner that multiple layers (for example, 100 layers) of each of these materials are formed thereon by way of a vapor deposition method, a sputtering method, or the like.

In connection with the above-described principle detection idea, a simulation was made under the following condition. In this simulation, $SiO_2$ was used as the base plate, and both $SiO_2$ and $Ti_2O_3$ were employed as the material layers. When laser light was entered into a multi-layer film sensor having a total number of 200 material layers (100 layers for each material), the below-mentioned results could be obtained. That is, an inclination of reflectance with respect to a change in wavelength of incident light was 2.8 dB/0.01 nm at the reflectance of 25%.

Thus, when a total layer number of the multi-layer films is increased, the reflectance becomes higher, and also, the reflectance changes steeply with respect to a change in the wavelengths of incident light, so that the sensitivity of the ultrasonic detecting element 2 can be increased.

By the way, in the multi-layer film sensor 20 shown in FIG. 2, the thickness of the multi-layer film 22 as an ultrasonic sensitive portion, namely, a length of a Bragg grating portion may be preferably made shorter than a length of an ultrasonic wavelength "$\lambda_s$" in the Bragg grating portion. Furthermore, the thickness of the multi-layer film 22 may be preferably made smaller than, or equal to approximately ¾ of the ultrasonic wavelength $\lambda_s$ in the Bragg grating portion. In this case, the ultrasonic wavelength "$\lambda_s$" of the Bragg grating portion is expressed by the below-mentioned expression (3):

(ultrasonic wavelength $\lambda_s$)=(sound velocity in Bragg grating portion)/(frequency of ultrasonic wave)     (3)

The reason why the length of this Bragg grating portion is thus limited is given as follows. That is, in the case where the length of the Bragg grating portion is larger than approximately ¾ of the ultrasonic wavelength $\lambda_s$ in the Bragg grating portion, waveform of a detection signal is distorted on the side of the lower frequency, as compared with waveform of actually received ultrasonic waves, and also a sensitivity of the multi-layer film sensor is lowered. This is caused by the following conceivable fact. That is, while the ultrasonic waves are propagated through the Bragg grating portion, such portions where expanding/compressing phases are inverted may be produced in the Bragg grating portion. As a result, when the entire sensor portion is observed, the expanding/compressing phases are offset.

To avoid such a phenomenon, the length of the Bragg grating portion must be made shorten than the ultrasonic wavelength propagated through the Bragg grating portion. Preferably, the length of the Bragg grating portion may be made shorter than, or equal to approximately ¾ of the ultrasonic wavelength, and more preferably may be made equal to an approximately ½ of the ultrasonic wavelength.

Figure 3A:
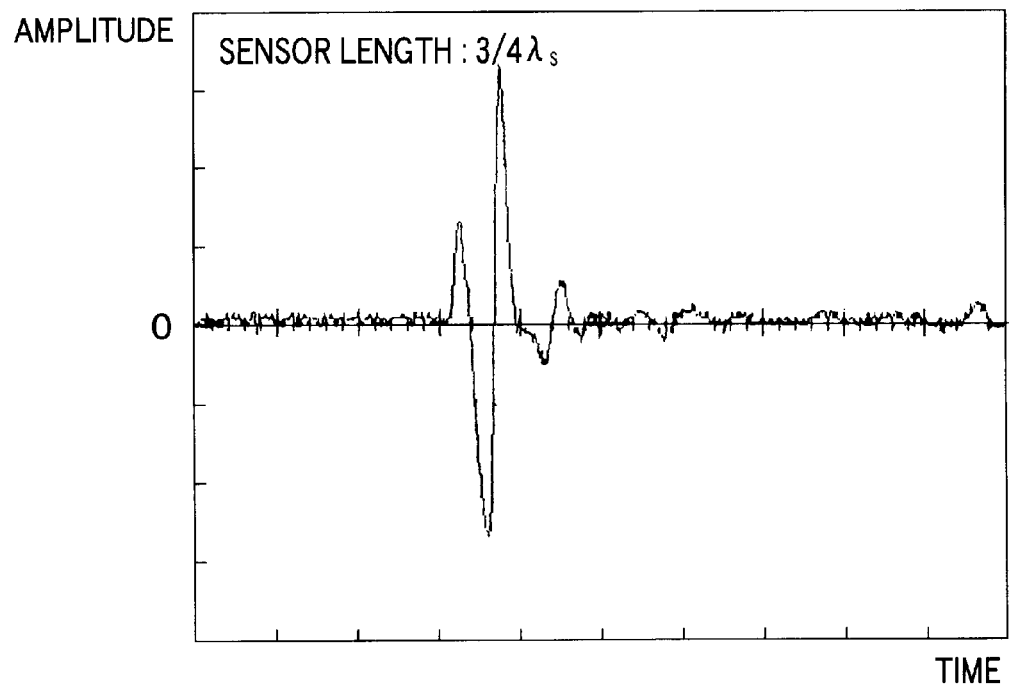
FIG. 3A and FIG. 3B are graphic diagrams for graphically showing experimental results obtained by applying ultrasonic waves to sensors having different sensor lengths and by monitoring detection signals obtained from the sensors.
Figure 3B:
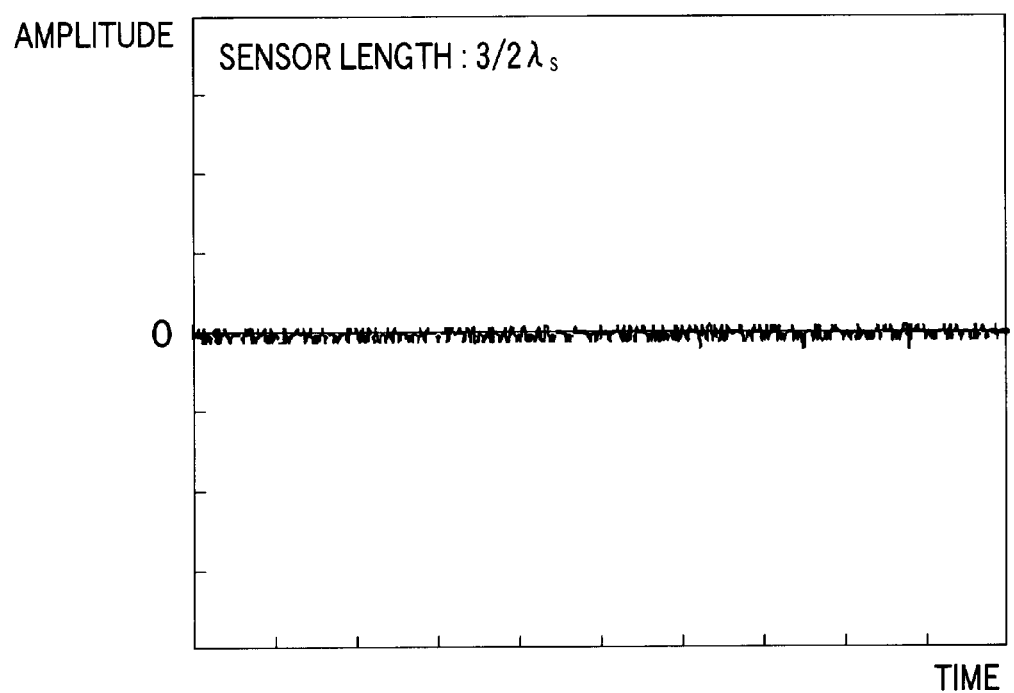

For instance, when ultrasonic waves in a frequency range of 3.5 MHz are applied to two sorts of Bragg gratings having a sensor length of ¾ $\lambda_s$ and another sensor length of ½ $\lambda_s$, waveforms of detection signals are derived from the respective sensors as shown in FIG. 3A and FIG. 3B. As shown in FIG. 3A, when the sensor length is ¾ $\lambda_s$, a detection signal having an amplitude which is changed in accordance with applied ultrasonic waves was monitored. To the contrary, as shown in FIG. 3B, when the sensor length is ⅔ $\lambda_s$, a change in an amplitude of a detection signal can not be substantially monitored. Thus, in the ultrasonic sensing portion having the Bragg grating structure, when the sensor length is made longer, the sensitivity of the sensor is considerably deteriorated.

Figure 4:
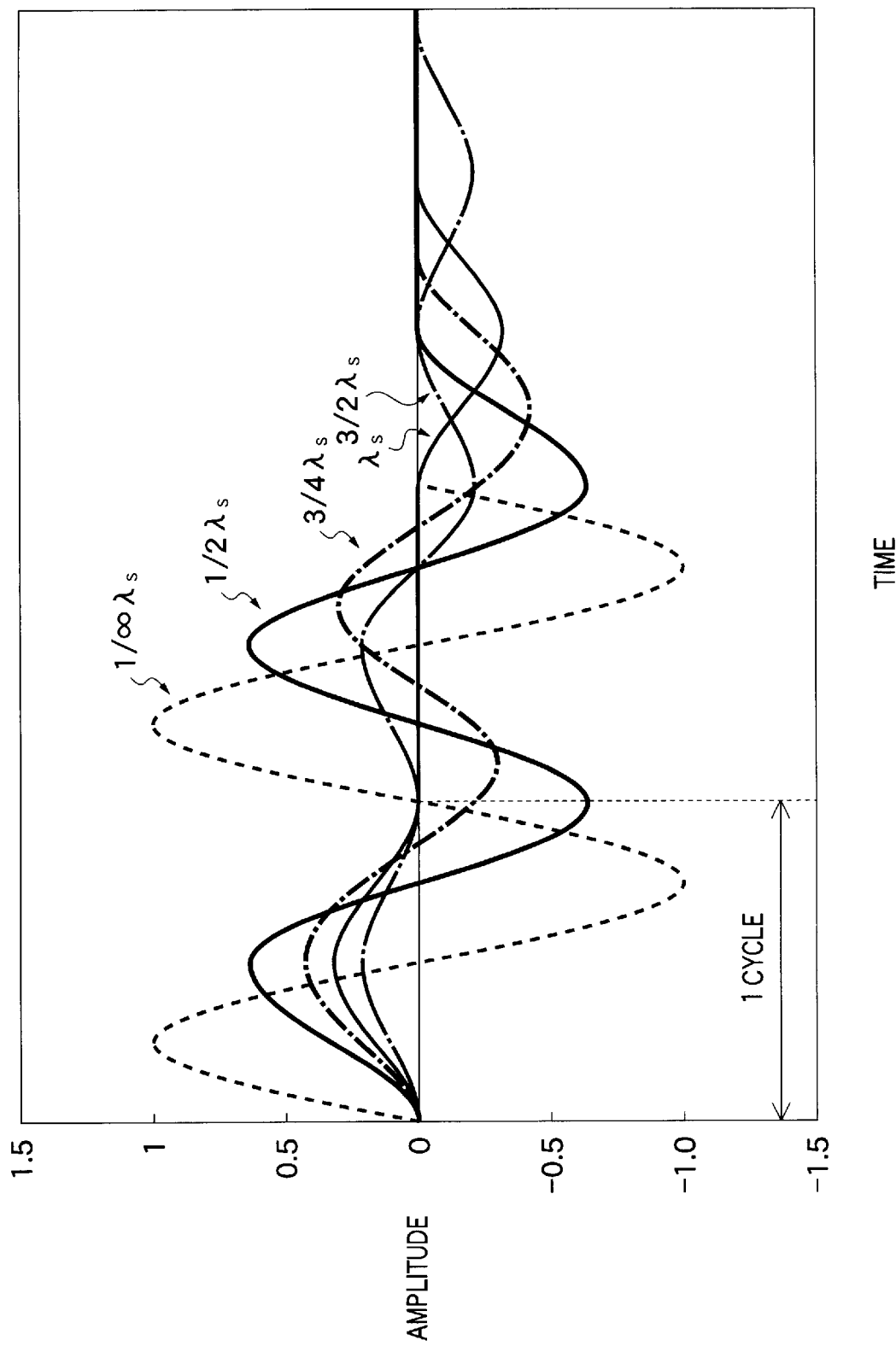
FIG. 4 is a graphic diagram for graphically showing a simulation result obtained by applying ultrasonic waves to the sensors having the different sensor lengths and by monitoring detection signals derived from the sensors.

When ultrasonic waves are applied to Bragg gratings having different sensor lengths respectively, such waveforms of sensor detection signals as shown in FIG. 4 are acquired. FIG. 4 shows a result of simulations executed on the basis of an assumption made as follows. That is, ultrasonic waves are applied to four sorts of sensors having sensor lengths of ½ $\lambda_s$, ¾ $\lambda_s$, $\lambda_s$, and ½ $\lambda_s$ over two time periods equivalent to two wavelengths of sine waves. In FIG. 4, a waveform when a sensor length is equal to (1/∞) $\lambda_s$, namely infinitely small corresponds to an ideal waveform indicative of the waveform of the ultrasonic wave for two time periods. To the contrary, as to waveforms obtained when other sensor lengths are employed, amplitudes of sensor detection signals are decreased in accordance with increases of sensor lengths, so that phases of these detection signals are delayed. When the sensor length is equal to "$\lambda_s$", such a portion that an amplitude becomes "0" is continued after a ½ wavelength has been detected. This is because while the ultrasonic waves are propagated through this sensor, such a condition is continued in which an average value of amplitudes existed in this sensor becomes zero. Furthermore, when the sensor length is equal to ½ $\lambda_s$, an amplitude is further decreased, and thus, the waveform is not analogous to the received waveform of the ultrasonic wave. Thus, performance of the sensor is deteriorated when the sensor length is prolonged. In order that a waveform of ultrasonic waves containing phases and amplitudes is faithfully reproduced by a signal detected from a sensor, a length of this sensor must be made infinitely short. However, as shown in FIG. 4, if such a detection signal having the waveform obtained when the sensor length is ¾ $\lambda_s$ can be acquired, a reception waveform of an ultrasonic wave may be reproduced by using phase distortion which has been previously acquired. Also, in a general-purpose ultrasonic receiving apparatus, since a detection signal is processed by executing a phase matching process operation and a low-pass filter process operation to produce an ultrasonic image, it is not necessary to reproduce a reception waveform of ultrasonic waves as the waveform of the detection signal when the detection signal is used to produce an ultrasonic image. For example, in the case where distortion of a detection signal corresponds to such a waveform distortion when the sensor length shown in FIG. 4 is ¾ $\lambda_s$, even if a reception waveform of ultrasonic waves is not completely reproduced, there is no practical problem. As a consequence, if the sensor length is shorter than, or equal to ¾ $\lambda_s$, it is so conceivable that such a detection signal capable of producing an ultrasonic image may be acquired.

For instance, in the case where a frequency of ultrasonic waves to be detected is 3.5 MHz, and a sound velocity within a material of a Bragg grating portion is 5500 m/s, a wavelength "$\lambda_s$" of ultrasonic waves which are propagated through the Bragg grating portion may be calculated as follows:

$\lambda_s = 5500/(3.5 \times 10^6) = 1571.4$ ($\mu$m)

As a consequence, an upper limited length of this Bragg grating portion may be calculated as follows:

$1571 \times (¾) = 1178.5$ ($\mu$m)

Accordingly, if the length of the Bragg grating portion is made shorter than, or equal to 1178.5 $\mu$m (for instance, approximately 1 mm), then it is possible to suppress adverse influences which are caused by inversions of expanding/compressing phases within the Bragg grating portion. Therefore, in particular, higher sensitivities can be obtained with respect to ultrasonic waves propagated from the vertical direction of the multi-layer film 22.

In the ultrasonic probe according to this first embodiment, another ultrasonic detecting element (etalon sensor) 24 as shown in FIG. 5 may be employed by substituting the above-described ultrasonic detecting element (multi-layer film sensor) 20 as shown in FIG. 2.

In the ultrasonic detecting element (etalon sensor) 24 of FIG. 5, a base plate 25 is such a film-shaped base plate which may be deformed by receiving ultrasonic waves. For example, this base plate 25 owns a circular shape having a diameter of approximately 2 cm or more. Another base plate 26 is arranged opposite to this base plate 25, which constitute a structure similar to that of an etalon.

Assuming now that a reflectance of the base plates 25 and 26 is "R", a distance between these base plates 25 and 26 is "d", and also a wavelength of incident light is "λ", a transmittance "T" of an etalon may be expressed by the below-mentioned expressions (4) and (5). In the expression (5), symbol "n" shows an arbitrary integer.

$$T=[1+4R/(1-R)^2 \cdot \sin^2(\phi/2)]^{-1} \quad (4)$$

$$\phi=2\pi/\lambda \cdot 2nd \cdot \cos\theta \quad (5)$$

In those expressions, symbol "θ" represents a projection angle which is measured from a vertical line of a projection plane. When this projection angle "θ" is equal to zero, the below-mentioned expression (6) may be obtained:

$$\phi=4\pi nd/\lambda \quad (6).$$

The etalon passes therethrough the light having the wavelength "λ" by the transmittance "T", and reflects thereon the light by the reflectance (1−T).

When ultrasonic waves are propagated through the ultrasonic detecting element 24, the base plate 25 is distorted, and the interval "d" between the base plate 25 and the base plate 26 is changed at respective positions of the reception plane, so that the reflectance of light having the wavelength "λ" is changed. A reflection characteristic of the etalon is changed in a periodic manner in accordance with the change in the wavelengths. When such a detection light having a center wavelength within a region where a changing rate of the reflection characteristic is large is entered into the base plate 26, when ultrasonic waves are applied to this base plate 26, a change in intensity of reflection light in accordance with strengths of ultrasonic waves at the respective positions of the reception plane may be monitored. Since this strength change in the reflection light is converted into strengths of ultrasonic waves, the strengths of the ultrasonic waves may be monitored in a two-dimensional manner.

Next, an ultrasonic probe according to a second embodiment of the present invention will now be explained. In this ultrasonic probe according to the second embodiment of the present invention, an ultrasonic reception plane of a plurality of ultrasonic transmitting elements is formed in such a manner that at least one ultrasonic transmitting element is surrounded by this ultrasonic reception plane.

Figure 6A:
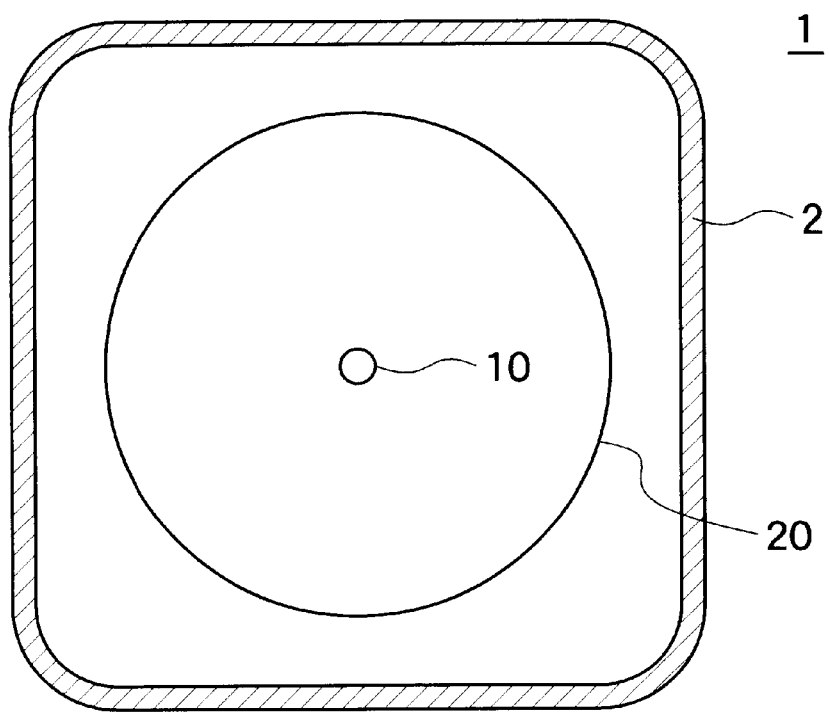
FIG. 6A and FIG. 6B are diagrams for schematically showing structures of ultrasonic probes according to a second embodiment of the present invention, i.e.
Figure 6B:
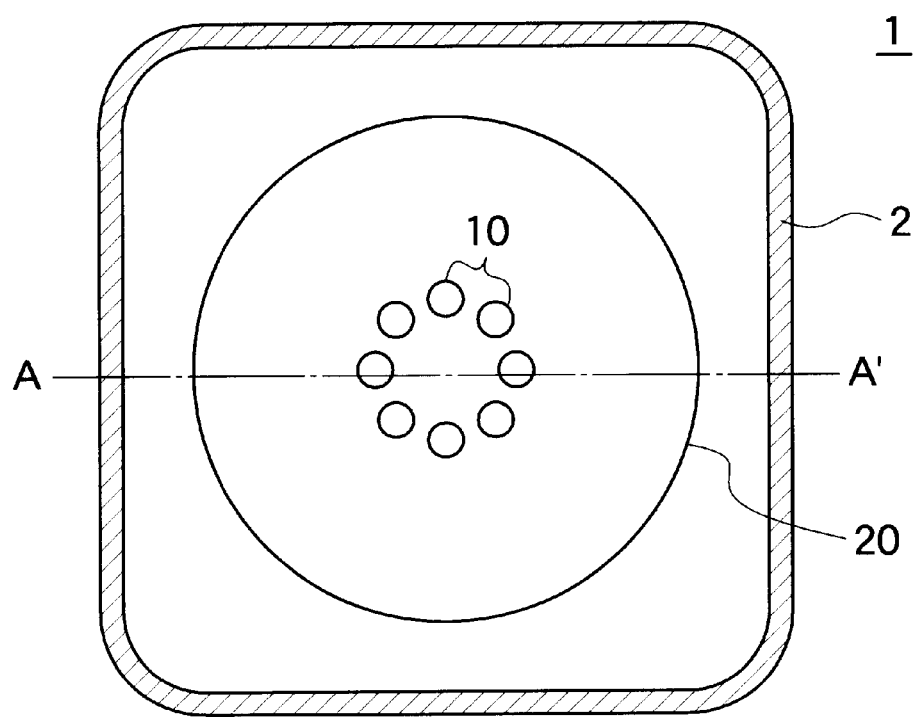

FIG. 6A and FIG. 6B are diagrams for schematically showing structures of ultrasonic probes according to the second embodiment of the present invention, i.e., FIG. 6A is a plan view for showing an internal structure within a housing of the ultrasonic probe having a single ultrasonic transmitting element, and FIG. 6B is a plan view for showing an internal structure within a housing of the ultrasonic probe having a plurality of ultrasonic transmitting elements. As shown in FIG. 6A and FIG. 6B, at least one ultrasonic transmitting element 10, and an ultrasonic detecting element 20 are mounted inside a housing 2 of an ultrasonic probe 1. In the case where one ultrasonic transmitting element 10 is arranged at a center of this ultrasonic detecting element 20, ultrasonic transmission beam scanning can not be performed, and therefore, an omnidirectional ultrasonic transmitting element may be preferably employed. On the other hand, in such a case where a plurality of ultrasonic transmitting elements 10 are arranged in either a one-dimensional manner or a two-dimensional manner inside the ultrasonic detecting element 20, ultrasonic transmission beam scanning can be performed in either a one-dimensional manner or a two-dimensional manner.

In this second embodiment, such an ultrasonic detecting element (multi-layer film sensor) 20 is employed as shown in FIG. 2. Alternatively, the ultrasonic detecting element (etalon sensor) 24 shown in FIG. 5 may be employed.

Figure 7A:
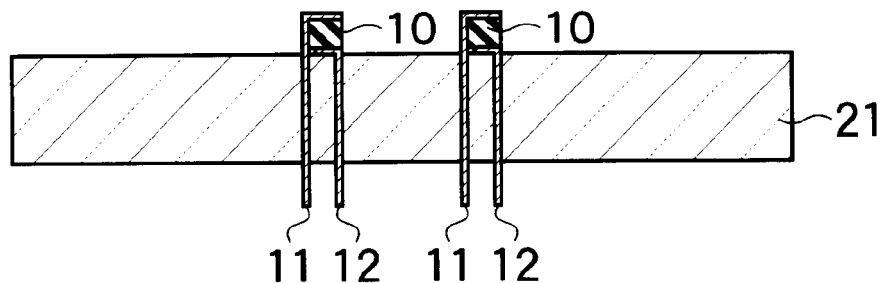
FIG. 7A to FIG. 7C are sectional views used to explain a first manufacturing method for manufacturing the ultrasonic probe according to the second embodiment of the present invention.
Figure 7B:
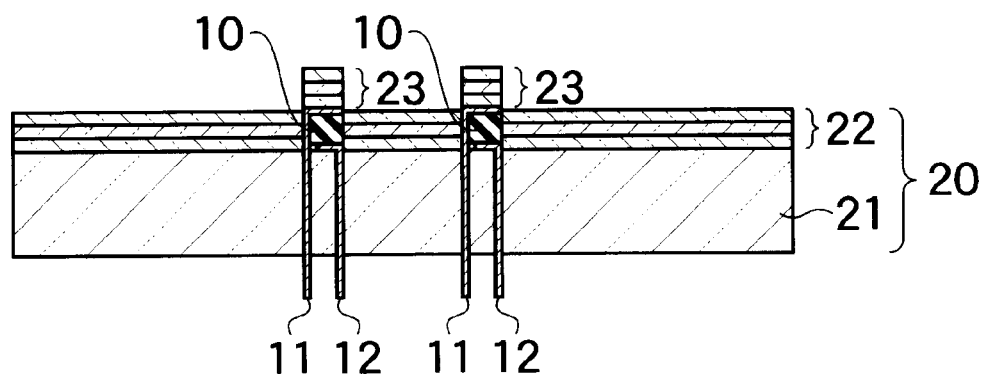
Figure 7C:
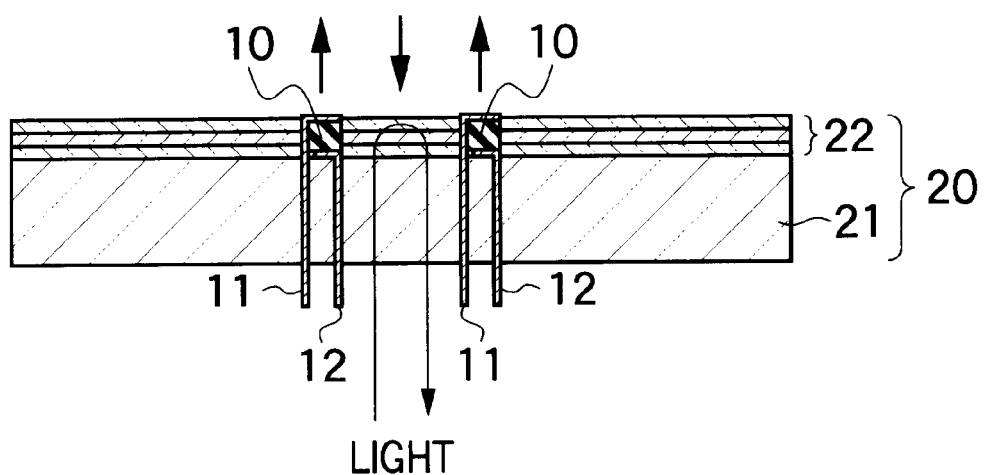

FIG. 7A to FIG. 7C are explanatory diagrams for explaining a first manufacturing method of the ultrasonic probe according to this second embodiment, and showing sectional views, taken along a plane A—A' of FIG. 6B.

First, as shown in FIG. 7A, an electrode 12, an ultrasonic transmitting element 10, and another electrode 11 are formed on a base plate 21 which is made of materials such optical glass as quartz glass ($SiO_2$) or BK7 (manufactured by Schott Glass). In this case, both the electrode 11 and the electrode 12 are manufactured in such a manner that these electrodes 11 and 12 break through the base plate 21 to the opposite side of this base plate 21.

Next, as shown in FIG. 7B, two sorts of materials having different refractive indexes are alternately stacked on a base plate 21 where an electrode 12, an ultrasonic transmitting element 10, and another electrode 11 have been formed, so that a multi-layer film 22 having a Bragg grating structure is formed. As two sorts of materials, for example, a combination of quartz glass ($SiO_2$) and a titanium oxide ($Ti_2O_3$) may be employed, and another combination of quartz glass ($SiO_2$) and a tantalum oxide ($Ta_2O_5$) may be used. The two sorts of material layers are manufactured by a vacuum deposition method, a sputtering method, or the like.

Subsequently, as shown in FIG. 7C, a multi-layer film 22 formed on an electrode 11 is removed by way of a selective etching method, or the like. As a result, a reception plane of an ultrasonic detecting element 20 is formed in such a manner that an ultrasonic transmitting element 10 is surrounded by this reception plane.

In this embodiment, the multi-layer film 22 is formed on the same side as the ultrasonic reception plane of the base plate 21. Alternatively, the multi-layer film 22 may be formed on the side opposite to the ultrasonic reception plane of the base plate 21.

Figure 8A:
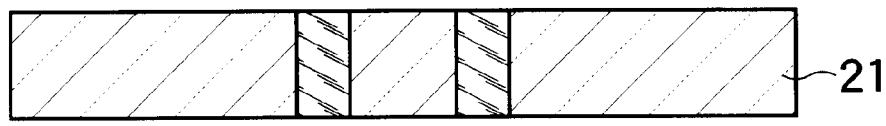
FIG. 8A to FIG. 8C are sectional views used to explain a second manufacturing method for manufacturing the ultrasonic probe according to the second embodiment of the present invention.
Figure 8B:
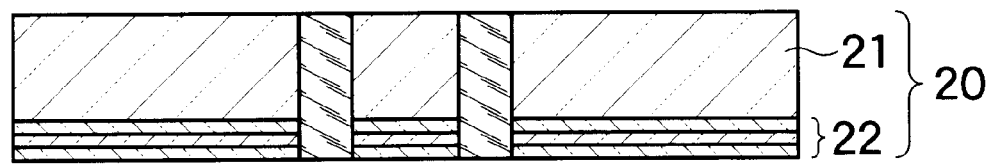
Figure 8C:
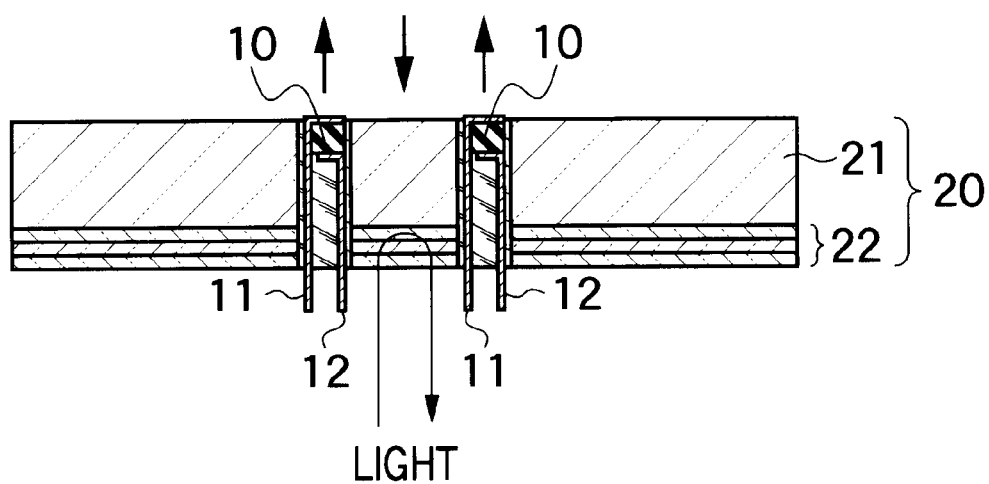

FIG. 8A to FIG. 8C are explanatory diagrams for explaining a second manufacturing method of the ultrasonic probe according to this embodiment, and show sectional views, taken along line A—A' of FIG. 6B.

First, as shown in FIG. 8A, a plurality of openings are formed in a base plate 21 made of such a material as optical glass.

Next, as shown in FIG. 8B, two sorts of materials having different refractive indexes are alternately stacked on a lower-sided plane of a base plate 21, as viewed in this drawing, so that a multi-layer film 22 having a Bragg grating structure is formed.

Next, as shown in FIG. 8C, an ultrasonic transmitting unit containing an electrode 11, an ultrasonic transmitting element 10, and another electrode 12 is inserted into an opening of a base plate 21. As a result, a reception plane of an ultrasonic detecting element 20 is formed in such a manner that the ultrasonic transmitting element 10 is surrounded by this reception plane.

Figure 9:
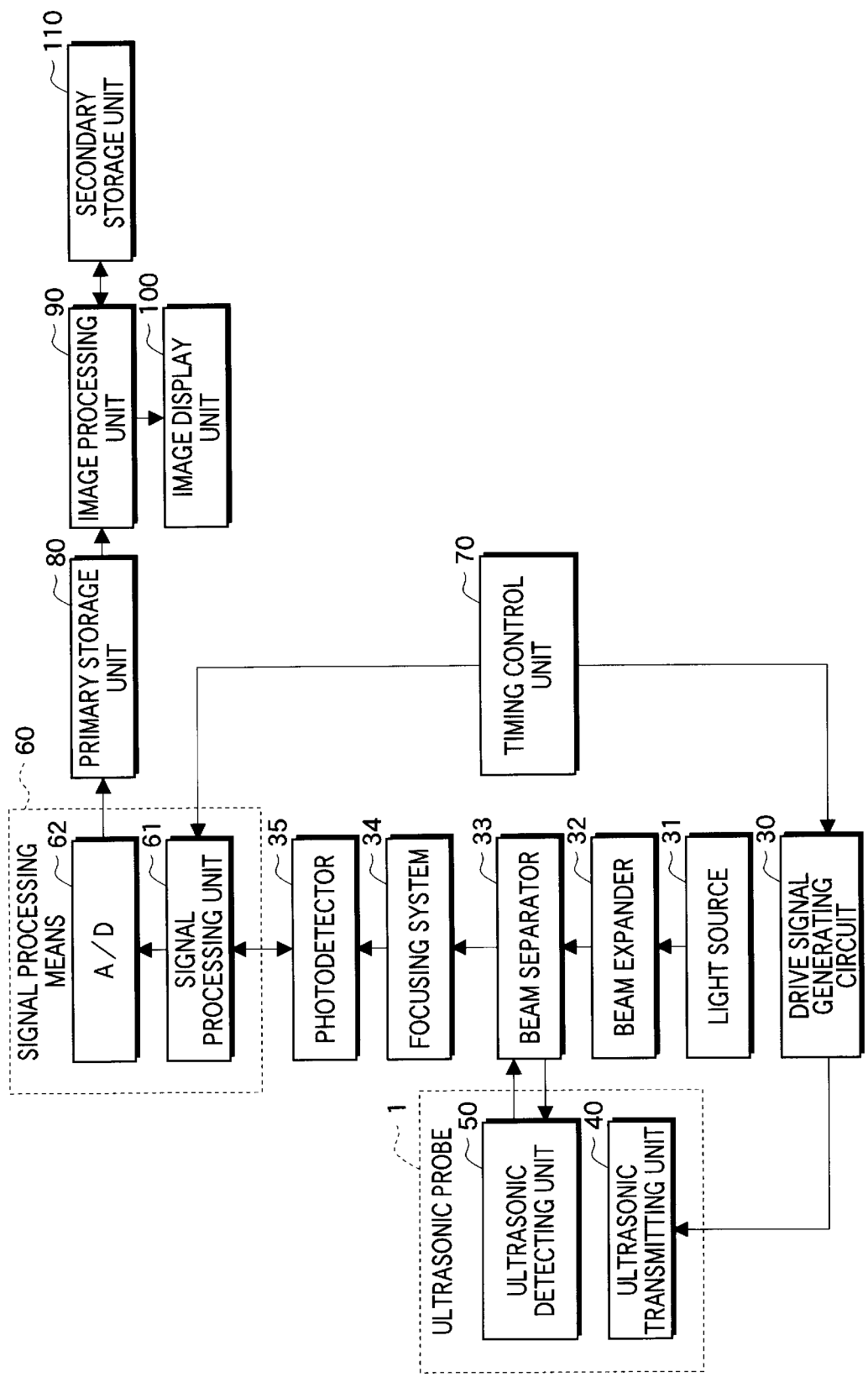
FIG. 9 is a schematic block diagram for showing an arrangement of an ultrasonic diagnosing apparatus according to another embodiment of the present invention.

Next, an ultrasonic diagnosing apparatus according to one embodiment of the present invention will be explained. FIG. 9 is a schematic block diagram for showing an arrangement of an ultrasonic diagnosing apparatus according to this embodiment. This ultrasonic diagnosing apparatus is accomplished by employing the above-described ultrasonic probe 1 according to the present invention. As shown in FIG. 9, the ultrasonic probe 1 includes both an ultrasonic transmitting unit 40 having an ultrasonic transmitting element, and an ultrasonic detecting unit 50 having an ultrasonic detecting element.

The ultrasonic diagnosing apparatus according to this embodiment includes a drive signal generating circuit 30, a light source 31, a beam expander 32, a beam separator 33, a focusing system 34, and a photodetector 35. Among these structural elements, both the beam expander 32 and the focusing system 34 correspond to arbitrary structural elements. The ultrasonic transmitting unit 40 transmits ultrasonic waves (ultrasonic beams) in accordance with drive signals generated from the drive signal generating circuit 30. The ultrasonic beams transmitted from the ultrasonic transmitting unit 40 are reflected from a diagnostic object, and then, the reflected ultrasonic beams (namely, ultrasonic echoes) are received by the ultrasonic detecting unit 50. While such light which has been produced from the light source 31 and has passed through the beam expander 32 and the beam separator 33 is entered into the ultrasonic detecting unit 50, this light is modulated on the basis of the ultrasonic beams applied to the ultrasonic detecting unit 50, and then, this modulated light is reflected from this ultrasonic detecting unit 50. The reflected light is entered via the beam separator 33 and the focusing system 34 into the photodetector 35 so as to be detected in a two-dimensional manner.

This ultrasonic diagnosing apparatus is further includes a signal processing means 60 having both a signal processing unit 61 and an A/D converter 62, a timing control unit 70, a primary storage unit 80, an image processing unit 90, an image display unit 100, and a secondary storage unit 110. A detection signal output from the photodetector 35 is entered into the signal processing unit 61, and this detection signal processed by the signal processing unit 61 is converted into a digital signal corresponding thereto by the A/D converter 62.

The timing control unit 70 controls the drive signal generating unit 30 to generate the drive signal at predetermined timing, and also controls the signal processing means 60 to receive a detection signal from the photodetector 35 after a constant time period has passed from a transmission time point. As previously explained, since the timing control unit 70 controls timing of the drive signal and the detection signal so as to limit a readout time range, so that reflections of ultrasonic waves from a specific depth of an object to be inspected can be optically detected.

The primary storage unit 80 stores thereinto plural frames of plane data acquired by the signal processing means 60. The image processing unit 90 reconstructs either two-dimensional data or three-dimensional data on the basis of these plane data, and also, executes such process operations as an interpolation process, a response modulation process, and a gradation process. The image display unit 100 corresponds to a display apparatus such as a CRT and an LCD, for example, and displays thereon an image on the basis of the image data to which these process operations have been carried out. Further, the secondary storage unit 110 stores thereinto data which has been processed by the image processing unit 90.

Figure 10:
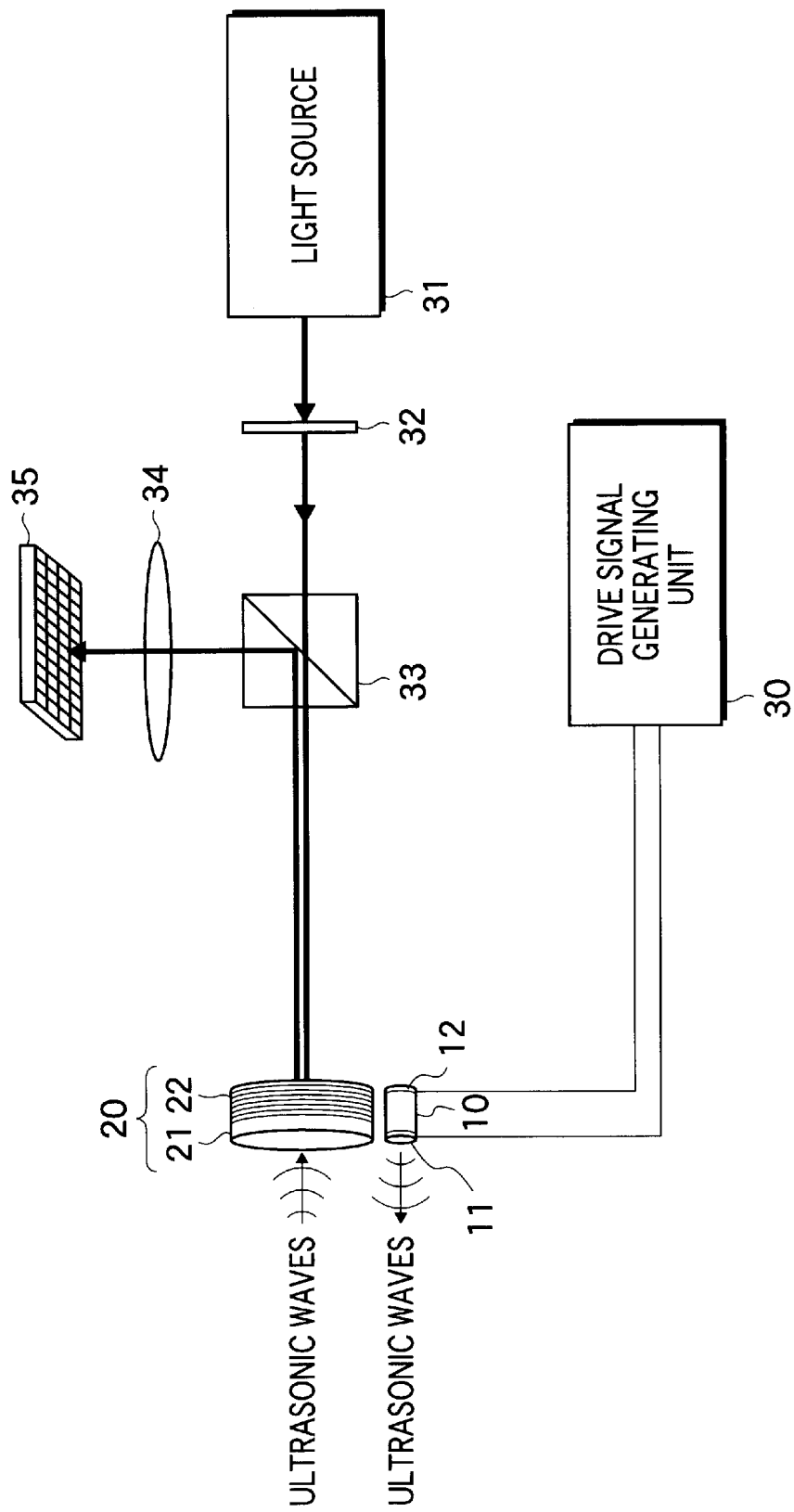
FIG. 10 is an explanatory diagram for explaining operations of the ultrasonic diagnosing apparatus according to this embodiment.

Referring now to FIG. 10, operations of the above-described ultrasonic diagnosing apparatus according to this embodiment will be described.

In FIG. 10, the drive signal generating circuit 30 generates either a pulse-shaped drive signal, or a continuous wave-shaped (CW-mode) drive signal. This drive signal is applied to the ultrasonic transmitting element 10 via both the electrodes 11 and 12, and thus, this ultrasonic transmitting element 10 transmits ultrasonic waves (ultrasonic beams) in accordance with this drive signal. The ultrasonic waves transmitted from the ultrasonic transmitting element 10 are reflected from the object to be inspected (diagnostic object), and then, ultrasonic echoes reflected from this object are received by the ultrasonic detecting element 20.

The light source 31 emits, for instance, single-mode laser light having a single wavelength of 500 nm to 1600 nm. The beam separator 33 is constructed by a half mirror, an optical circulator, a polarization beam splitter, or the like. This beam separator 33 may pass therethrough incident light entered from a first direction toward a second direction, and furthermore, may pass therethrough reflection light returned from the second direction toward a third direction which is different from the first direction. In this embodiment, a half mirror is employed as the beam separator 33. This half mirror 33 may pass therethrough incident light, and may reflect thereon reflection light which is returned from a direction opposite to the incident direction, so that this reflected light is propagated to a direction at substantially 90 degrees with respect to the incident direction. Alternatively, in this case, before the incident light passes the beam separator 33 along the light propagation direction, this incident light may be expanded by a beam expander 32.

The ultrasonic detecting element 20 includes a base plate 21 and multi-layer films 22 stacked on this base plate 21. The ultrasonic detecting element 20 has a wave receiving plane which may produce distortion by receiving propagated ultrasonic waves. The ultrasonic detecting element 20 modulates light on the basis of ultrasonic waves applied to the base plate 21 to reflect the modulated light. This light is emitted from the light source 31, and then penetrates the beam separator 33, and thereafter, is entered into the multi-layer films 22. The light, which is reflected from the ultrasonic detecting element 20, is further reflected on the beam separator 33, and this reflected light is entered into the photodetector 35 having a plurality of pixels.

The photodetector 35 corresponds to a two-dimensional array detector which is constituted by a CCD, an MOS type sensor, a plurality of PD (photodiodes) or the like. The photodetector 35 detects such light with respect to each of pixels, while this light is entered from a position corresponding to the ultrasonic detecting elements 20 via the beam separator 33. This photodetector 35 outputs detection signals in accordance with strengths of light at the respective pixels. In this case, the reflection light may be directly entered into the photodetector 35, or may be entered via an optical fiber, or the like into the photodetector 35. Further, while the focusing system 34 such as a lens or the like is provided at a rear stage of the beam separator 33, the reflection light may be focused via this focusing system 34 onto the photodetector 35.

As previously described in detail, according to the present invention, since the ultrasonic detecting element having the ultrasonic receiving plane, which corresponds to a plurality of pixels of the photodetector, is employed, ultrasonic waves can be detected in a two-dimensional manner without necessities of the electric wiring works to the large number of very fine elements and without increasing of crosstalk and electric impedance. Furthermore, since the ultrasonic transmitting element is arranged at an internal portion or a peripheral portion of the ultrasonic detecting element, the ultrasonic probe equipped with the ultrasonic transmitting/receiving function can be manufactured in low cost. As a consequence, by using an ultrasonic diagnosing apparatus to which such an ultrasonic probe has been applied, either two-dimensional or three-dimensional ultrasonic images having better image qualities can be acquired.

What is claimed is:

1. An ultrasonic diagnosing apparatus comprising:
   an ultrasonic probe including at least one ultrasonic transmitting element for transmitting ultrasonic waves in accordance with a drive signal, and an ultrasonic detecting element having a reception plane surrounding said at least one transmitting element and capable of receiving ultrasonic waves and an ultrasonic sensing portion which is expanded and contracted by ultrasonic waves received at respective positions of said reception plane to change optical reflectances at corresponding positions of said ultrasonic sensing portion in accordance with expansion and contraction thereby modulating light on the basis of ultrasonic waves received at the respective positions of said reception plane;

a drive signal generating circuit for generating a drive signal to be applied to said at least one ultrasonic transmitting element;

a photodetector having a plurality of pixels, for detecting light output from corresponding positions of said ultrasonic detecting element to output detection signals;

signal processing means for receiving detection signals output from said photodetector to process the received detection signals;

control means for controlling both generation timing of said drive signals and reception timing of said detection signals;

image processing means for constructing an image signal on the basis of an output signal of said signal processing means; and an image display unit for displaying thereon an image on the basis of said image signal.

2. An ultrasonic diagnosing apparatus according to claim 1, wherein:

said at least one ultrasonic transmitting element includes a piezoelectric element for transmitting ultrasonic waves in accordance with a drive signal.

3. An ultrasonic diagnosing apparatus according to claim 1, wherein:

said photodetector includes any one of a CCD (charge-coupled device), an MOS (metal oxide semiconductor) type sensor, and a plurality of photodiodes.

4. An ultrasonic probe comprising:

an ultrasonic detecting element having a reception plane capable of receiving ultrasonic wave and an ultrasonic sensing portion which is expanded and contracted by ultrasonic waves received at respective positions of said reception plane to change optical reflectances at corresponding positions of said ultrasonic sensing portion in accordance with expansion and contraction thereby modulating light on the basis of ultrasonic waves received at the respective positions of said reception plane; and at least one ultrasonic transmitting element for transmitting ultrasonic waves.

5. An ultrasonic probe according to claim 4, wherein:

said reception plane of said ultrasonic detecting element is formed to surround at least one ultrasonic transmitting element.

6. An ultrasonic probe according to claim 4, wherein:

a length of said ultrasonic sensing portion of said ultrasonic detecting element is not larger than ¾ of a wavelength of ultrasonic waves which propagate through said ultrasonic sensing portion.

7. An ultrasonic probe according to claim 4, wherein: said at least one ultrasonic transmitting element includes a piezoelectric element for transmitting ultrasonic waves in accordance with a drive signal.

8. An ultrasonic probe comprising an ultrasonic detecting element having a reception plane capable of receiving ultrasonic waves, for modulating light on the basis of ultrasonic waves received at respective positions of said reception plane, said ultrasonic detecting element including a multi-layer film formed by alternately stacking two sorts of materials having different refractive indexes from each other; and at least one ultrasonic transmitting element for transmitting ultrasonic waves.

9. An ultrasonic probe according to claim 8, wherein:

said two sorts of materials have refractive indexes which are different from each other by at least 10%.

10. An ultrasonic probe according to claim 8, wherein:

layers of said two sorts of materials which constitute said multi-layer film include a layer having a film thickness of ¼ of a wavelength of light entered into said multi-layer film.

11. An ultrasonic probe according to claim 10, wherein:

layers of said two sorts of materials which constitute said multi-layer film further include a layer having a film thickness of ½ of a wavelength of light entered into said multi-layer film.

12. An ultrasonic probe comprising an ultrasonic detecting element having a reception plane capable of receiving ultrasonic waves, for modulating light on the basis of ultrasonic waves received at respective positions of said reception plane, said ultrasonic detecting element including two films located opposite to each other with a predetermined interval therebetween; and at least one ultrasonic transmitting element for transmitting ultrasonic waves.

13. An ultrasonic diagnosing apparatus comprising:

an ultrasonic probe including an ultrasonic detecting element having a reception plane capable of receiving ultrasonic waves, for modulating light on the basis of ultrasonic waves received at respective positions of said reception plane, and a plurality of ultrasonic transmitting elements arranged around the reception plane of said ultrasonic detecting element, for transmitting ultrasonic waves in accordance with drive signals;

a drive signal generating circuit for generating drive signals to be applied to said plurality of ultrasonic transmitting elements;

a photodetector having a plurality of pixels, for detecting light output from corresponding positions of said ultrasonic detecting element to output detection signals;

signal processing means for receiving detection signals output from said photodetector to process the received detection signals;

control means for controlling both generation timing of said drive signals and reception timing of said detection signals;

image processing means for constructing an image signal on the basis of an output signal of said signal processing means; and an image display unit for displaying thereon an image on the basis of said image signal.

14. An ultrasonic diagnosing apparatus according to claim 13, wherein:

said ultrasonic detecting element includes a multi-layer film formed by alternately stacking two sorts of materials having different refractive indexes from each other.

15. An ultrasonic diagnosing apparatus according to claim 13, wherein:

said ultrasonic detecting element includes two films located opposite to each other with a predetermined interval therebetween.

16. An ultrasonic diagnosing apparatus according to claim 13, wherein:

each of said plurality of ultrasonic transmitting elements includes a piezoelectric element for transmitting ultrasonic waves in accordance with a drive signal.

17. An ultrasonic diagnosing apparatus according to claim 13, wherein:

said photodetector includes any one of a CCD (charge-coupled device), an MOS (metal oxide semiconductor) type sensor, and a plurality of photodiodes.

18. An ultrasonic diagnosing apparatus comprising:

an ultrasonic probe including at least one ultrasonic transmitting element for transmitting ultrasonic waves in accordance with a drive signal, and an ultrasonic detecting element having a reception plane surrounding said at least one transmitting element and capable of receiving ultrasonic waves, for modulating light on the basis of ultrasonic waves received at the respective positions of said reception plane, said ultrasonic detecting element including a multi-layer film formed by alternately stacking two sorts of materials having different refractive indexes from each other;

a drive signal generating circuit for generating a drive signal to be applied to said at least one ultrasonic transmitting element;

a photodetector having a plurality of pixels, for detecting light output from corresponding positions of said ultrasonic detecting element to output detection signals;

signal processing means for receiving detection signals output from said photodetector to process the received detection signals;

control means for controlling both generation timing of said drive signals and reception timing of said detection signals;

image processing means for constructing an image signal on the basis of an output signal of said signal processing means; and an image display unit for displaying thereon an image on the basis of said image signal.

19. An ultrasonic diagnosing apparatus comprising an ultrasonic probe including at least one ultrasonic transmitting element for transmitting ultrasonic waves in accordance with a drive signal, and an ultrasonic detecting element having a reception plane surrounding said at least one transmitting element and capable of receiving ultrasonic waves, for modulating light on the basis of ultrasonic waves received at the respective positions of said reception plane, said ultrasonic detecting element including two films located opposite to each other with a predetermined interval therebetween;

a drive signal generating circuit for generating a drive signal to be applied to said at least one ultrasonic transmitting element;

a photodetector having a plurality of pixels, for detecting light output from corresponding positions of said ultrasonic detecting element to output detection signals;

signal processing means for receiving detection signals output from said photodetector to process the received detection signals;

control means for controlling both generation timing of said drive signals and reception timing of said detection signals;

image processing means for constructing an image signal on the basis of an output signal of said signal processing means; and an image display unit for displaying thereon an image on the basis of said image signal.

20. An ultrasonic probe comprising:

an ultrasonic detecting element having a reception plane capable of receiving ultrasonic waves, for modulating light on the basis of ultrasonic waves received at respective positions of said reception plane; and a plurality of ultrasonic transmitting elements, arranged around the reception plane of said ultrasonic detecting element, for transmitting ultrasonic waves.

* * * * *